(12) United States Patent
Nie (10) Patent No.: US 12,288,361 B2
(45) Date of Patent: Apr. 29, 2025

(54) POSITIONING AND TRACKING MEMBER, METHOD FOR RECOGNIZING MARKER, STORAGE MEDIUM, AND ELECTRONIC DEVICE

(71) Applicant: BOE Technology Group Co., Ltd., Beijing (CN)

(72) Inventor: Liping Nie, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 574 days.

(21) Appl. No.: 17/639,220

(22) PCT Filed: Mar. 16, 2021

(86) PCT No.: PCT/CN2021/081170
§ 371 (c)(1),
(2) Date: Feb. 28, 2022

(87) PCT Pub. No.: WO2021/185260
PCT Pub. Date: Sep. 23, 2021

(65) Prior Publication Data
US 2022/0405965 A1 Dec. 22, 2022

(30) Foreign Application Priority Data
Mar. 17, 2020 (CN) .......................... 202010186662.8

(51) Int. Cl.
*G06T 7/73* (2017.01)
*A61B 34/10* (2016.01)
(Continued)

(52) U.S. Cl.
CPC ................ *G06T 7/75* (2017.01); *A61B 34/10* (2016.02); *A61B 90/39* (2016.02); *G06T 7/149* (2017.01);
(Continued)

(58) Field of Classification Search
CPC ........... G06T 7/75; G06T 7/149; G06T 17/00; G06T 2207/10081; G06T 2207/30004;
(Continued)

(56) References Cited

U.S. PATENT DOCUMENTS 8,548,563 B2 * 10/2013 Simon .................... A61B 90/36
600/414
2008/0319313 A1 12/2008 Boivin et al.
(Continued)

FOREIGN PATENT DOCUMENTS

CN 1711968 A 12/2005
CN 1758284 A 4/2006
(Continued)

OTHER PUBLICATIONS

CN202010186662.8 first office action.
(Continued)

*Primary Examiner* — Oneal R Mistry
*Assistant Examiner* — Jongbong Nah
(74) *Attorney, Agent, or Firm* — IPro, PLLC (57) ABSTRACT

A positioning and tracking member is provided. The positioning and tracking member includes: a holding plate and a plurality of markers, wherein the holding plate comprises a first surface and a second surface that are opposite to each other, and the plurality of markers are disposed on the first surface, the second surface being configured to be adhered to a surface of a target object. A method for recognizing a maker, a storage medium, and an electronic device are also provided.

19 Claims, 4 Drawing Sheets

(51) Int. Cl.
*A61B 90/00* (2016.01)
*G06T 7/149* (2017.01)
*G06T 17/00* (2006.01)

(52) U.S. Cl.
CPC ........ *G06T 17/00* (2013.01); *A61B 2034/102* (2016.02); *A61B 2090/3937* (2016.02); *A61B 2090/3983* (2016.02); *G06T 2207/10081* (2013.01); *G06T 2207/30004* (2013.01); *G06T 2207/30204* (2013.01)

(58) Field of Classification Search
CPC . G06T 2207/30204; G06T 2207/30208; G06T 7/136; G06T 7/187; G06T 7/11; A61B 34/10; A61B 90/39; A61B 2034/102; A61B 2090/3937; A61B 2090/3983; A61B 2034/2055; A61B 2090/367; A61B 34/20; A61B 2034/2059; G06V 10/26; G06V 20/64; G06V 2201/03
See application file for complete search history.

(56) References Cited

U.S. PATENT DOCUMENTS

| | | | | |
|---|---|---|---|---|
| 2015/0057675 | A1 | 2/2015 | Akeel et al. | |
| 2015/0327948 | A1* | 11/2015 | Schoepp | A61B 5/061 600/424 |
| 2018/0035964 | A1* | 2/2018 | Funabasama | G16H 50/30 |
| 2018/0092699 | A1* | 4/2018 | Finley | A61B 34/20 |
| 2019/0298277 | A1 | 10/2019 | Zhang et al. | |
| 2019/0357884 | A1 | 11/2019 | Williams et al. | |
| 2020/0022615 | A1* | 1/2020 | Schoepp | A61B 5/061 |

FOREIGN PATENT DOCUMENTS

| | | | | |
|---|---|---|---|---|
| CN | 101533518 | A | | 9/2009 |
| CN | 102147919 | A | | 8/2011 |
| CN | 102319116 | A | | 1/2012 |
| CN | 103654965 | A | | 3/2014 |
| CN | 103679810 | A | | 3/2014 |
| CN | 104331924 | A | | 2/2015 |
| CN | 105055021 | A | | 11/2015 |
| CN | 105055022 | A | * | 11/2015 |
| CN | 105078577 | A | | 11/2015 |
| CN | 205215355 | U | | 5/2016 |
| CN | 205514897 | U | | 8/2016 |
| CN | 106139423 | A | | 11/2016 |
| CN | 106388849 | A | | 2/2017 |
| CN | 106890031 | A | | 6/2017 |
| CN | 107182200 | A | | 9/2017 |
| CN | 107468351 | A | | 12/2017 |
| CN | 107596578 | A | | 1/2018 |
| CN | 108053433 | A | | 5/2018 |
| CN | 108670301 | A | | 10/2018 |
| CN | 108852496 | A | | 11/2018 |
| CN | 109091229 | A | * | 12/2018 ............ A61B 34/20 |
| CN | 109952070 | A | | 6/2019 |
| CN | 110163867 | A | | 8/2019 |
| CN | 110400286 | A | | 11/2019 |
| CN | 209673111 | U | | 11/2019 |
| CN | 110570515 | A | | 12/2019 |
| CN | 110706241 | A | | 1/2020 |
| CN | 111388092 | A | | 7/2020 |

OTHER PUBLICATIONS

CN202010186662.8 second office action.
CN202010186662.8 third office action.
CN202010186662.8 fourth office action.
Wang, Matthew Y., et al. "An automatic technique for finding and localizing externally attached markers in CT and MR volume images of the head." IEEE Transactions on Biomedical Engineering 43.6 (1996): 627-637.
Chen, Dingguo, et al. "Automatic fiducial localization in brain images." International Journal of Computer Assisted Radiology and Surgery 1 (2006): 45.
Zhou, Z-H. "Automatic registration of markers in medical image." Chinese Journal of Biomedical Engineering 22.5 (2003): 438-442.

* cited by examiner

POSITIONING AND TRACKING MEMBER, METHOD FOR RECOGNIZING MARKER, STORAGE MEDIUM, AND ELECTRONIC DEVICE

CROSS-REFERENCE TO RELATED APPLICATION

This application is a U.S. national stage of international application No. PCT/CN2021/081170, filed on Mar. 16, 2021, which claims priority to Chinese Patent Application No. 202010186662.8, field on Mar. 17, 2020 and entitled "POSITIONING TRACKING MEMBER, METHOD FOR RECOGNIZING POSITIONING SPHERE, STORAGE MEDIUM, AND ELECTRONIC DEVICE," the disclosures of which are herein incorporated by reference in their entireties.

TECHNICAL FIELD

The present disclosure relates to the field of medical navigation technologies, and in particular, relates to a positioning and tracking member, a method for recognizing a marker, a storage medium, and an electronic device.

BACKGROUND

A working flow of a navigation system in the medical field generally includes medical imaging, preoperative surgical path planning, intraoperative patient image space registration, intraoperative positioning and navigating, and postoperative effect evaluation, wherein intraoperative patient image space registration, also known as surgical registration, is one of the key technologies in navigation, the precision of registration directly affecting a final treatment outcome of a surgery.

SUMMARY

According to embodiments of the present disclosure, a positioning and tracking member, a method for recognizing a marker, a storage medium, and an electronic device are provided.

According to an aspect of the embodiments of the present disclosure, a positioning and tracking member is provided. The positioning and tracking member includes a holding plate and a plurality of markers, wherein the holding plate includes a first surface and a second surface that are opposite to each other, and the plurality of markers are disposed on the first surface, the second surface being configured to be adhered to a surface of a target object.

In some embodiments, a difference between an eigenvalue of the holding plate in a medical image and an eigenvalue of the surface of the target object in the medical image is greater than a threshold.

In some embodiments, the holding plate is made of polyvinyl chloride.

In some embodiments, the first surface is provided with a plurality of grooves, wherein the plurality of grooves are in one-to-one correspondence with the plurality of markers, and the markers are light-reflective spheres, one part of the light-reflective sphere being disposed within a corresponding groove of the plurality of grooves, and other part of the light-reflective sphere protruding from the first surface.

In some embodiments, the plurality of markers are arranged in an array, and a spacing between any two adjacent markers of the plurality of markers is in a range of 15 mm to 50 mm.

According to another aspect of the embodiments of the present disclosure, a method for recognizing a marker is further provided. The method includes: acquiring a three-dimensional medical model of the positioning and tracking member as defined in the above embodiments, wherein the positioning and tracking member is adhered to a surface of a target object; acquiring a plurality of candidate connected regions by performing image segmentation on the three-dimensional medical model; and determining, based on geometrical information of each of the candidate connected regions, a target connected region corresponding to the marker from the plurality of candidate connected regions.

In some embodiments, acquiring the three-dimensional medical model of the positioning and tracking member includes: acquiring a two-dimensional scanned image of the positioning and tracking member captured by a medical imaging device; and acquiring the three-dimensional medical model by performing three-dimensional reconstruction on the two-dimensional scanned image.

In some embodiments, acquiring the plurality of candidate connected regions by performing image segmentation on the three-dimensional medical model includes: acquiring a binarization model by performing threshold segmentation on the three-dimensional medical model based on eigenvalues of various voxels in the three-dimensional medical model; and determining the plurality of candidate connected regions based on non-zero voxels in the binarization model.

In some embodiments, the three-dimensional medical model includes a plurality of layers; and determining the plurality of candidate connected regions based on non-zero voxels in the binarization model includes: determining the non-zero voxels in a plurality of layers in the binarization model by traversing the plurality of layers in the binarization model; and determining the plurality of candidate connected regions based on coordinates of the non-zero voxels.

In some embodiments, the three-dimensional medical model is a three-dimensional medical model of computed tomography (CT), and the eigenvalues are CT values.

In some embodiments, determining, based on the geometrical information of each of the candidate connected regions, the target connected region corresponding to the marker from the plurality of candidate connected regions includes: comparing the geometrical information of each of the candidate connected regions with an actual size of the marker; and determining a candidate connected region, where a difference value between the geometrical information and the actual size is within a predetermined range, of the plurality of candidate connected regions, as the target connected region.

In some embodiments, prior to acquiring the plurality of candidate connected regions by performing image segmentation on the three-dimensional medical model, the method further includes: filtering the three-dimensional medical model.

According to another aspect of the embodiments of the present disclosure, an apparatus for recognizing a marker is further provided. The apparatus includes: an acquiring module, configured to acquire a three-dimensional medical model of the positioning and tracking member as defined in the above embodiments, wherein the positioning and tracking member is adhered to a surface of a target object; a segmenting module, configured to acquire a plurality of candidate connected regions by performing image segmentation on the three-dimensional medical model; and a determining module, configured to determine, based on geometrical information of each of the candidate connected regions, a target connected region corresponding to the marker from the plurality of candidate connected regions.

In some embodiments, the acquiring module includes: an acquiring sub-module, configured to acquire a two-dimensional scanned image of the positioning and tracking member captured by a medical imaging device; and a reconstructing sub-module, configured to acquire the three-dimensional medical model by performing three-dimensional reconstruction on the two-dimensional scanned image.

In some embodiments, the segmenting module includes: a segmenting sub-module, configured to acquire a binarization model by performing threshold segmentation on the three-dimensional medical model based on eigenvalues of various voxels in the three-dimensional medical model; and a determining sub-module, configured to determine the plurality of candidate connected regions based on non-zero voxels in the binarization model.

In some embodiments, the three-dimensional medical model includes a plurality of layers, and the determining sub-module is configured to determine the non-zero voxels in a plurality of layers in the binarization model by traversing the plurality of layers in the binarization model; and determine the plurality of candidate connected regions based on coordinates of the non-zero voxels.

In some embodiments, the three-dimensional medical model is a three-dimensional medical model of CT, and the eigenvalues are CT values.

In some embodiments, the determining module is configured to compare the geometrical information of each of the candidate connected regions with an actual size of the marker; and determine, a candidate connected region, where a difference value between the geometrical information and the actual size is within a predetermined range, of the plurality of candidate connected regions, as the target connected region.

In some embodiments, the apparatus further includes: a filtering module, configured to filter the three-dimensional medical model before the segmenting module acquires the plurality of candidate connected regions by performing image segmentation on the three-dimensional medical model.

According to another aspect of the embodiments of the present disclosure, a non-transitory storage medium is further provided. The storage medium stores a computer program, wherein the computer program, when run by a processor, causes the processor to perform any of the methods described above.

According to another aspect of the embodiments of the present disclosure, an electronic device is further provided. The electronic device at least includes a memory storing a computer program therein and a processor, wherein the processor, when running the computer program in the memory, is caused to perform any of the methods described above.

DETAILED DESCRIPTION

Intraoperative patient image space registration includes: firstly, a support of a marker is fixed to a patient's bone through the skin, such that the marker is rigidly connected to but independent of a human body; then, an image including the marker is acquired through scanning and capturing by an imaging device; and finally, positions and coordinates of the marker in image space are determined.

Figure 1:
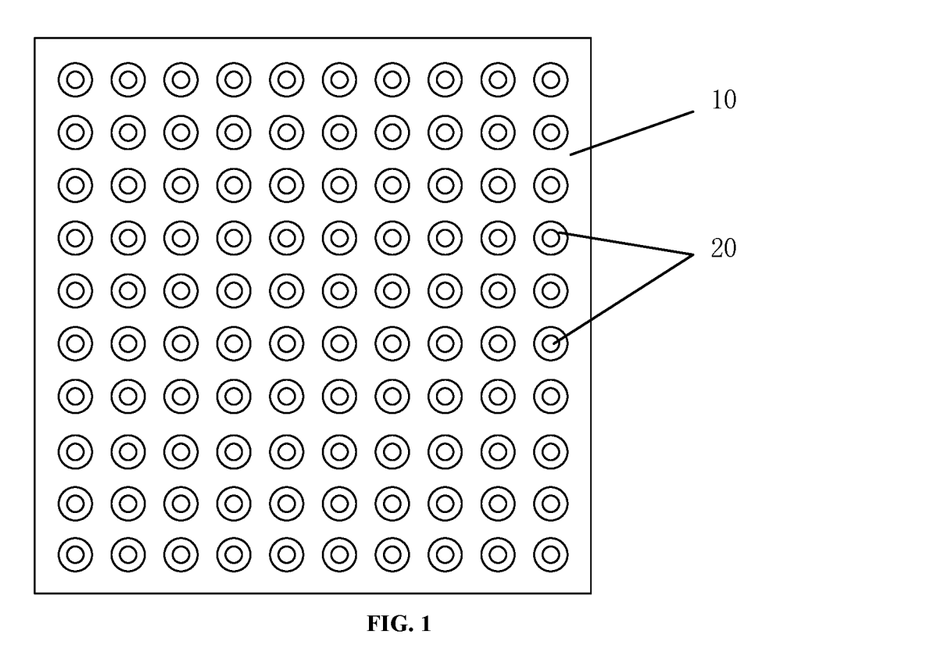
FIG. 1 shows a top-view structural schematic diagram of a positioning and tracking member according to an embodiment of the present disclosure.

A positioning and tracking member is provided in an embodiment of the present disclosure, FIG. 1 shows a schematic diagram of the positioning and tracking member according to the embodiment of the present disclosure. As shown in FIG. 1, the positioning and tracking member includes a holding plate 10 and a plurality of markers 20. The plurality of markers 20 are disposed on the holding plate 10.

In an embodiment of the present disclosure, the number of the markers 20 and an arrangement fashion of the markers 20 may be set depending on actual needs, which are not limited in the embodiment of the present disclosure. For example, as shown in FIG. 1, the holding plate 10 is provided with 100 markers. The 100 markers 20 are arranged in an array (arranged in a 10*10 array as shown in FIG. 1). In other embodiments, the plurality of markers 20 may also be arranged in concentric circles of different radii, or arranged in other desired arrangement fashions.

In an exemplary embodiment, a spacing between any two adjacent markers 20 is in a range of 15 mm to 50 mm. For example, the spacing between any two adjacent markers 20 is 30 mm.

Figure 2:
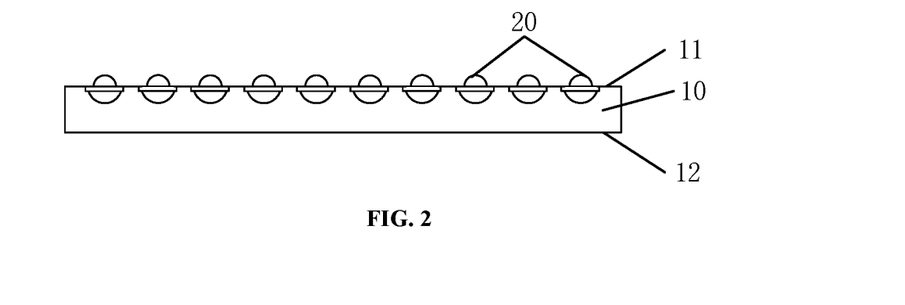
FIG. 2 shows an assembled structural schematic diagram of the positioning and tracking member shown in FIG. 1.

FIG. 2 is an assembled structural schematic diagram of the positioning and tracking member shown in FIG. 1. In conjunction with FIG. 2, the holding plate 10 includes a first surface 11 and a second surface 12 that are opposite to each other. The plurality of markers 20 are disposed on the first surface, and the second surface 12 is configured to be adhered to a surface of a target object. In an embodiment of the present disclosure, the surface of the target object may be a human skin surface.

In some examples, the markers 20 are embedded in the first surface. Still referring to FIG. 2, the first surface 11 of the holding plate 10 is provided with a plurality of grooves. The plurality of grooves are in one-to-one correspondence with the plurality of markers 20.

In FIG. 2, the markers 20 are light-reflective spheres. One part of the light-reflective spheres is disposed within a corresponding groove of the plurality of grooves, and the other part of the light-reflective spheres protrudes from the first surface 11.

The positioning and tracking member in this embodiment is placed on a body site to be detected of a patient during use (for example, the positioning and tracking member may be placed on the back of the patient in the case that surgery is needed for the back of the patient), such that a medical imaging device and an optical tracking device can be simultaneously used to perform scanning and tracking.

In an exemplary embodiment, the light-reflective spheres can reflect infrared light, and thus can be detected by an optical tracker during surgical navigation. It should be noted that shapes of the markers are not limited in the embodiments of the present disclosure, as long as the markers can be detected by both the medical imaging device and the optical tracking device.

In order to distinguish the positioning and tracking member from a human tissue structure in a medical image captured by the medical imaging device, there is a need to select suitable material for the positioning and tracking member, to ensure that the positioning and tracking member and the human tissue structure have different eigenvalues in the medical image.

In some examples, assuming that the medical imaging device is a computed tomography (CT) device, a corresponding eigenvalue is a Hu value or a CT value.

In some examples, the holding plate 10 is made of polyvinyl chloride (PVC). The difference between a Hu value of PVC and a Hu value of a human body is large, such that the human skin may be distinguished clearly from the positioning and tracking member in a CT image, thereby improving the precision of image recognition.

In some examples, the markers 20 are made of materials that are recognizable by both the medical imaging device and the optical tracking device. The precision of registration for coordinate systems of two different devices may also be improved through respective recognition for the same positioning and tracking member under two different coordinate systems.

Figure 3:
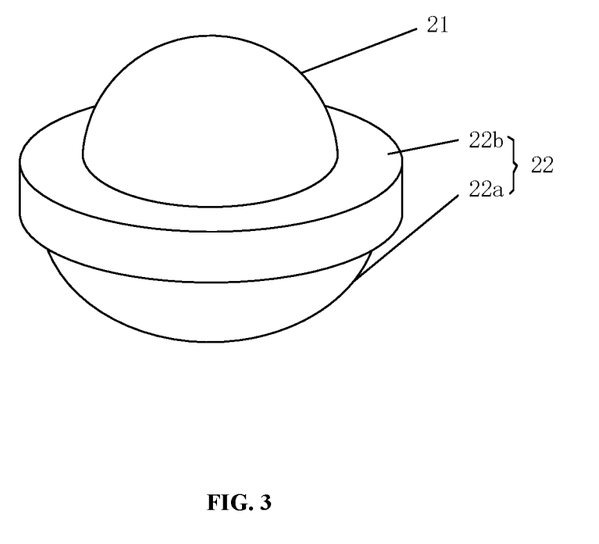
FIG. 3 shows a schematic diagram of a stereo-structure of a light-reflective sphere according to an embodiment of the present disclosure.

In an embodiment of the present disclosure, for shapes of the light-reflective spheres, a regular spherical member may be used, or an irregular spherical member as shown in FIG. 3 may be used.

FIG. 3 shows a schematic structural diagram of a light-reflective sphere according to an embodiment of the present disclosure. As shown in FIG. 3, the light-reflective sphere includes a sphere body 21 and a base 22. The sphere body 21 is fixedly connected to the base 22. For example, the sphere body 21 is adhered to the base 22. The sphere body 21 is made of a transparent material of a refractive index, for example, glass. A reflecting layer (not shown in the figure) is provided between the sphere body 21 and the base 22. In an exemplary embodiment, the reflecting layer may be a metal layer. The base 22 includes an arc-shaped base body 22a and an outer flange 22b disposed on an outer peripheral wall of the arc-shaped base body 22a.

The outer flange is disposed on the outer peripheral wall of the arc-shaped base body 22a, and a groove is provided in the holding plate 10 correspondingly, thereby facilitating the positioning and mounting of the light-reflective sphere. In some examples, the light-reflective sphere is connected to the holding plate 10 by an adhesive or the like.

Figure 4:
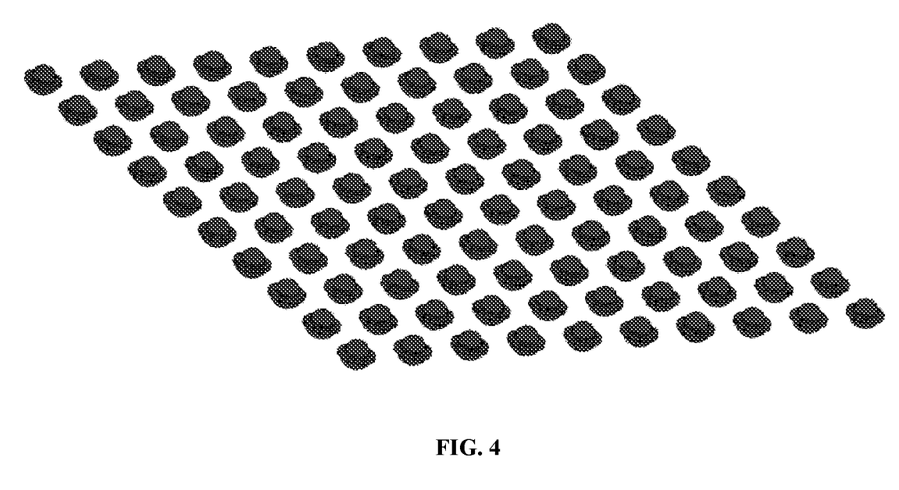
FIG. 4 shows a schematic diagram of imaging of a positioning and tracking member according to an embodiment of the present disclosure.

An image of an irregular light-reflective sphere upon scanning and recognition is shown in FIG. 4 (only an image of the light-reflective sphere is shown in FIG. 4). The light-reflective sphere has an irregular shape, such that it is convenient to distinguish the light-reflective sphere from the human tissue in the image, thereby facilitating subsequent registration as well.

In some other examples, a sphere center of the light-reflective sphere may also be made of an imaging material such as metal, and then a reflective material is coated on an outer surface of the light-reflective sphere, such that the light-reflective sphere may be recognized by both the medical imaging device and the optical tracking device.

According to this embodiment, a positioning and tracking member is provided. The positioning and tracking member may be used as a positioning member for both the medical imaging device and the optical tracking device, and may be configured to cover the body of the patient directly during use, without damages to the body of the patient, thereby improving usage experience of the patient, and achieving better surgical effects.

According to an embodiment of the present disclosure, a method for recognizing a marker is further provided. The method is, based on the above-mentioned positioning and tracking member, used to recognize a position of the marker of the positioning and tracking member in an image space. The image space in this embodiment is a coordinate space of an image captured by the medical imaging device. Only in the case that the position and coordinates of the marker in the image space are accurately determined, subsequent registration operation between the image space and an actual surgical space can be performed conveniently, so as to ensure accurate navigation for devices such as a surgical robot.

Figure 5:
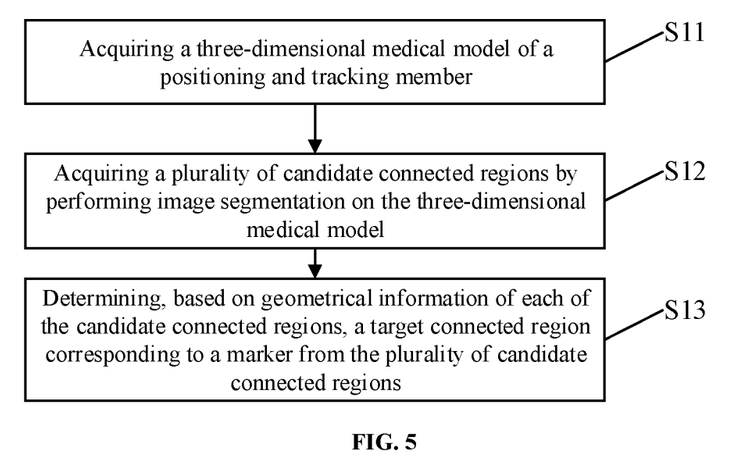
FIG. 5 shows a flowchart of a method for recognizing a marker according to an embodiment of the present disclosure.

FIG. 5 is a flowchart of a method for recognizing a marker according to an embodiment of the present disclosure. As shown in FIG. 5, the method includes the following processes.

In S11, a three-dimensional medical model of a positioning and tracking member is acquired.

In an embodiment of the present disclosure, the three-dimensional medical model of the positioning and tracking member refers to a three-dimensional model acquired by scanning a target object, to which the positioning and tracking member is adhered, using a medical imaging device. In an exemplary embodiment, the medical imaging device is a CT device, a magnetic resonance imaging (MRI) device, etc.

In S12, a plurality of candidate connected regions is acquired by performing image segmentation on the three-dimensional medical model.

In an embodiment of the present disclosure, the fashion of image segmentation is not limited, such as the image segmentation may be threshold based image segmentation, region growing based image segmentation, etc., as long as connected regions corresponding to different objects can be determined.

In S13, a target connected region corresponding to the marker is determined from the plurality of candidate connected regions based on geometrical information of each of the candidate connected regions.

By placing the positioning and tracking member on the body of the patient directly, a rigid connection between the positioning and tracking member and the human body is not needed, thereby avoiding damages to the human body. Furthermore, in an algorithm for recognizing the marker, recognition of the marker in the image space can be achieved rapidly by comparing the geometrical information of various candidate connected regions in the three-dimensional medical model with an actual size of the marker, with fast recognition speed and high recognition accuracy.

Figure 6:
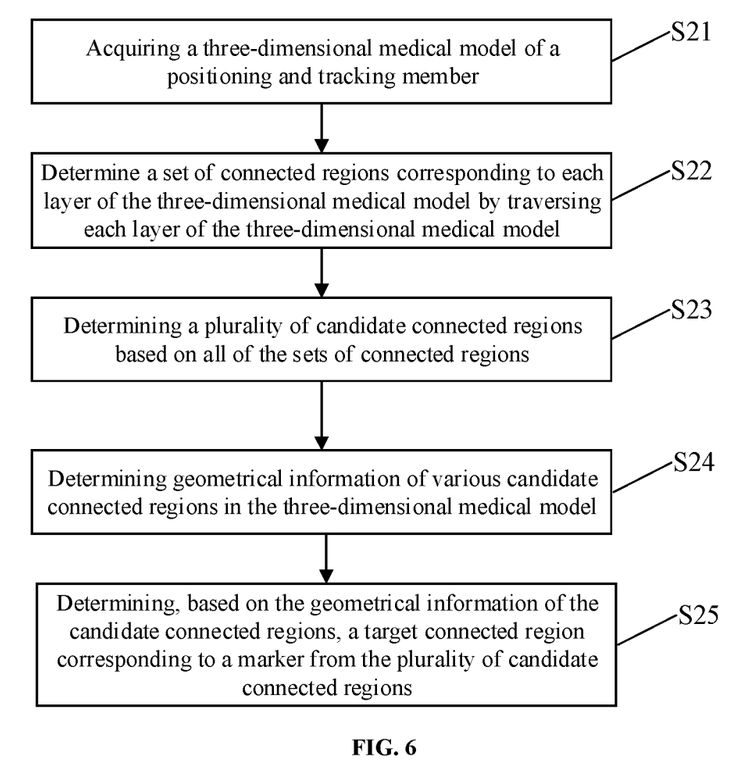
FIG. 6 shows a flowchart of another method for recognizing a marker according to an embodiment of the present disclosure.

FIG. 6 is a flowchart of another method for recognizing a marker according to an embodiment of the present disclosure. As shown in FIG. 6, the method includes the following processes.

In S21, a three-dimensional medical model of a positioning and tracking member is acquired.

In an exemplary embodiment, the process S21 includes acquiring a two-dimensional scanned image of the positioning and tracking member and determining the three-dimensional medical model of the positioning and tracking member based on the two-dimensional scanned image.

In practical use, the positioning and tracking member is placed (for example, adhered) near a site, where surgery is to be performed, of the human body (for example, the positioning and tracking member is placed on the back of the patient), and then two-dimensional scanned images of the site to be detected of the patient and the positioning and tracking member is acquired by scanning and capturing the patient using the medical imaging device.

Generally, the medical imaging device may capture a plurality of images at the same time, or the medical imaging device may perform slow-moving and scanning during scanning the site to be detected of the patient, and capture an image once at a short interval during moving, so as to finally acquire a plurality of images of the site to be detected. In an embodiment of the present disclosure, the images captured by the medical imaging device include a two-dimensional scanned image of the positioning and tracking member.

The three-dimensional medical model of the positioning and tracking member is acquired by performing three-dimensional reconstruction on the two-dimensional scanned images described above. In an exemplary embodiment, a marching cubes algorithm may be used in this embodiment to reconstruct the three-dimensional medical model.

In an exemplary embodiment, the medical imaging device is a CT device or an MRI device. In this embodiment, the CT device is taken as an example for exemplary illustration.

In S22, a set of connected regions corresponding to each layer of the three-dimensional medical model is determined by traversing each layer of the three-dimensional medical model.

In this embodiment, the three-dimensional medical model includes a plurality of layers. Each layer may be a piece of two-dimensional scanned image constituting the three-dimensional medical model, or the plurality of layers are layers acquired by re-dividing a reconstructed three-dimensional medical model. In an exemplary embodiment, each layer corresponds to a layer of voxels.

Each layer is traversed, so as to determine all connected regions in each layer, and form a set of connected regions corresponding to each layer. A binarization three-dimensional medical model (briefly referred to as a binarization model) may be acquired in the case that each layer is traversed.

In an exemplary embodiment, determining all connected regions in each layer, and forming the set of connected regions corresponding to each layer includes: performing image segmentation on each layer to determine the set of connected regions in each layer.

In an exemplary embodiment, image segmentation is performed by threshold segmentation. Herein, the threshold segmentation refers to determining mark values of various voxels based on a relationship between eigenvalues corresponding to various voxels in the three-dimensional medical model and a threshold. For example, in the case that an eigenvalue corresponding to a voxel is within a set range of thresholds, a mark value of the voxel is determined to be 1; and in the case that an eigenvalue corresponding to a voxel is beyond the set range of thresholds, a mark value of the voxel is determined to be 0. In this way, the mark values of the various voxels in the three-dimensional medical model are all 1 or 0, such that binarization layers are acquired. In an exemplary embodiment, the set range of thresholds is determined based on the eigenvalue of the positioning and tracking member.

In an embodiment of the present disclosure, the three-dimensional medical model consists of a plurality of voxels each having a corresponding eigenvalue. For example, for a CT image, the eigenvalue of each voxel is a Hu value. In an exemplary embodiment, a range of thresholds is set to be a range of 140 to 200.

For example, in a first layer of the three-dimensional medical model, contents captured include the skin, bones, and organs of the patient as well as the markers and the holding plate, which are represented with different Hu values on the layer due to intrinsic density differences between these contents, therefore boundaries between images of different tissues or components are formed. Presented by the tissues or components described above on the layer are all connected regions. For example, the light-reflective sphere may be represented as a circle in the layer, and the organs may be represented in a shape of some cross section in the layer. It should be understood that coordinates of any point in each connected region may be determined based on the coordinate system in the image space, and the number of points within the connected region may be determined based on the coordinates of each point, such that the area of each connected region may be determined.

In some examples, each point within the connected regions corresponds to a voxel in the three-dimensional medical model.

In an exemplary embodiment, during the traversing for each layer, non-zero voxels in each layer are marked first, and then, a set of connected regions corresponding to each layer is determined based on coordinates of all of the non-zero voxels in each layer.

In some examples, for the reconstructed three-dimensional medical model, the three-dimensional model may be segmented based on predetermined band-pass thresholds, wherein the band-pass thresholds include $T_{high}$ and $T_{low}$, specific values of which are adjusted depending on a Hu value presented by the material of the holding plate. Performing segmentation based on the band-pass thresholds aims to separate a positioning and tracking member from the body site of the patient based on high Hu values of the holding plate and a light-reflective sphere, so as to reduce the amount of data for subsequent processing. For example, assuming that the Hu value of the human skin is 100, the Hu value of the light-reflective sphere is 150, and the Hu value of the holding plate is 190, the band-pass thresholds may be set to be $T_{high}$=140 and $T_{low}$=200. A part with a Hu value between 140 to 200 is segmented from the three-dimensional model. The segmented part of the model mainly consists of the light-reflective sphere and the holding plate, but may also include some other components or other human tissue structures with the Hu values between 140 to 200. Therefore, subsequent processing is needed.

On this basis, filtering may further be performed on the three-dimensional medical model to eliminate impacts of noise points, in the segmented three-dimensional medical model, on subsequent processing, thereby improving the precision of recognition, wherein the filtering used in this embodiment is filtering based on median values.

It should be understood that in practical use, the three-dimensional medical model may be filtered upon segmentation, or segmented upon filtering, which is not limited in this embodiment.

It should be noted that in a possible implementation, the light-reflective sphere is adhered to the holding plate by an adhesive. The difference between the Hu value of the adhesive and the Hu value of the holding plate is large, such that the light-reflective sphere and the holding plate may correspond to different connected regions in the case that image segmentation is performed using the band-pass thresholds.

In S23, a plurality of candidate connected regions are determined based on all of the sets of connected regions.

Based on a sequential relationship between various layers in the three-dimensional medical model, upon acquiring all sets of connected regions corresponding to various layers by traversing all of the layers, the sets of connected regions between all of the layers are integrated based on coordinates of various connected regions of the sets of connected regions, so as to form a stereo-connected candidate connected regions.

In an embodiment of the present disclosure, for determining the candidate connected regions in the three-dimensional medical model, the connected regions in adjacent layers are connected mainly based on coordinates of various connected regions of all of the sets of connected regions in the image space, such that the connected regions belonging to the same issue or component in practice are enabled to form, in the three-dimensional model, the candidate connected regions corresponding to the issue or component.

Taking the light-reflective sphere as an example, an entity of the light-reflective sphere is necessarily presented in a plurality of successive layers upon scanning, and an image presented thereby in each layer is a circular connected region. Points that corresponds to each other in a plurality of circular connected regions described above may have different X-axis coordinates and Y-axis coordinates in the three-dimensional medical model, but necessarily have a unique Z-axis coordinate (for example, a Z-axis coordinate corresponding to a sphere center of the light-reflective sphere). Furthermore, all of the connected regions described above have the same Hu value. At this point, the connected regions in a plurality of layers may be considered to be the connected regions belonging to the same issue or component. The connected regions are associated to form an entire closed sphere body, which is a candidate connected region. The connected regions between all of the layers in the three-dimensional medical model are associated based on the fashion described above to determine all of the candidate connected regions in the three-dimensional medical model.

With S22 and S23, the plurality of candidate connected regions are acquired by performing image segmentation on the three-dimensional medical model. It should be noted that in this embodiment, the image segmentation based on the threshold segmentation is taken as an example for illustration, and in other embodiments, other image segmentation fashions may also be employed, as long as the plurality of candidate connected regions can be acquired.

In S24, geometrical information of each of the candidate connected regions in the three-dimensional medical model is determined.

In S24, the geometrical information of each of the determined candidate connected regions is determined based on voxels included in the candidate connected regions and corresponding coordinates of the voxels, wherein the geometrical information of the candidate connected region includes at least one of the volume, the length, the width, and the height of the connected region.

In an embodiment of the present disclosure, the volume of the candidate connected region may be represented by the number of the voxels included in the candidate connected region.

In the case that all of the candidate connected regions are determined, the geometrical information corresponding to each of the candidate connected regions may be determined based on coordinates of various voxels in the candidate connected regions. It should be noted that because the shape and size of each candidate connected region in the three-dimensional medical model are not regular, all of the candidate connected regions cannot be represented using a same standard representation fashion. Therefore, the length, the width, and the height used in this embodiment are employed as geometrical information, wherein a length of a vertical projection of a candidate connected region onto an X-axis is taken as the length of the candidate connected region, a length of a vertical projection of the candidate connected region onto a Y-axis is taken as the width of the candidate connected region, and a length of a vertical projection of the candidate connected region onto a Z-axis is taken as the height of the candidate connected region, such that the candidate connected regions of irregular shapes are represented in this fashion, so as to facilitate subsequent screening for a target connected region.

In S25, a target connected region corresponding to a marker is determined from the plurality of candidate connected regions based on the geometrical information of the candidate connected regions.

The marker is scanned and captured by the medical imaging device, and the size of the candidate connected region corresponding to the marker in the three-dimensional medical model should be the same as the actual size of the marker. Therefore, in order to recognize the target connected region corresponding to the marker in all of the candidate connected regions in the three-dimensional medical model, it is successively determined in this embodiment, based on the actual size of the marker, whether the geometrical information of various candidate connected regions meets a predetermined condition, to screen connected regions meeting the predetermined condition as the target connected regions. Voxels included in the target connected regions constitute the image of the marker in the image space.

In an exemplary embodiment, in S25, the geometrical information of various candidate connected regions are compared with the actual size of the light-reflective sphere first, and then a candidate connected region with a difference value between the geometrical information and the actual size within a predetermined range is taken as the target connected region.

It should be noted that the actual size of the marker is represented in this embodiment in a fashion the same as the fashion in which the geometrical information of the candidate connected regions are represented. That is, the lengths of the vertical projections of the marker onto the X-axis, Y-axis, and Z-axis are used as the actual sizes of the marker. The comparison can be done by means of subtraction. Taking the geometrical information including length, width, and height as an example, it may be detected that whether difference values between the length, the width, and the height of a connected region and actual length, width, and height of the marker are within a predetermined threshold, and then only a candidate connected region, whose difference values of the length, the width, and the height thereof are all within the preset threshold, can be used as the target connected region.

In practice, taking the light-reflective sphere of the shape shown in FIG. 3 as an example, the radius of upper half of the light-reflective sphere is 4.573 millimeters, the thickness of the outer flange is 2 millimeters, the diameter of the outer flange is 14.55 millimeters, and the radius of the lower half of the light-reflective sphere is 6.725 millimeters. Lengths of vertical projections onto the X-axis, Y-axis, and Z-axis corresponding to these parameters are 14.55 millimeters, 14.55 millimeters, and 13.298 millimeters. Because the size of a connected region, corresponding to the light-reflective sphere, in the three-dimensional medical model is the same as the actual size of the light-reflective sphere, the predetermined threshold may be set to be 2 millimeters in this embodiment. That is, in the case that a difference value between geometrical information of a candidate connected region and the actual size of the light-reflective sphere is within 2 millimeters, the candidate connected region may be considered to be an image corresponding to the light-reflective sphere, and may be used as the target connected region.

In order to facilitate a subsequent process of registration, upon recognizing image and specific positions of the candidate connected regions corresponding to various markers in the image space, the specific positions of various markers in the image space may be represented using coordinates of set points of the markers in the image space. For example, for the light-reflective sphere, a specific position of the light-reflective sphere in the image space may be represented using coordinates of the sphere center of the light-reflective sphere. Coordinates of other positions may also be selected depending on actual situations to represent the specific position of the light-reflective sphere in the image space, which is not limited in this embodiment.

By placing the positioning and tracking member on the body of the patient directly, a rigid connection between the positioning and tracking member and the human body is avoided, thereby avoiding damages to the human body. Furthermore, in the recognizing algorithm for the marker, recognition of the marker in the image space can be achieved rapidly by comparing the geometrical information of various connected regions in the three-dimensional medical model with the actual size of the marker, with fast recognition speed and high recognition accuracy.

Figure 7:
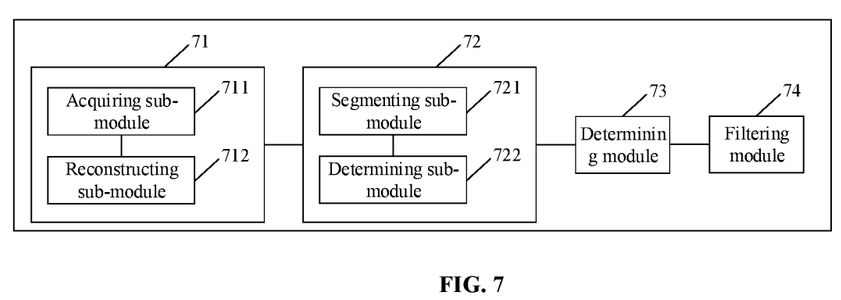
FIG. 7 shows a structural diagram of another apparatus for recognizing a marker according to an embodiment of the present disclosure.

According to an embodiment of the present disclosure, an apparatus for recognizing a marker is further provided. As shown in FIG. 7, the apparatus includes an acquiring module 71, a segmenting module 72, and a determining module 73. The acquiring module 71 is configured to acquire a three-dimensional medical model of a positioning and tracking member, wherein the positioning and tracking member is any of the above-mentioned positioning and tracking members and adhered to a surface of a target object. The segmenting module 72 is configured to acquire a plurality of candidate connected regions by performing image segmentation on the three-dimensional medical model. The determining module 73 is configured to determine, based on geometrical information of each of the candidate connected regions, a target connected region corresponding to the marker from the plurality of candidate connected regions.

Optionally, the acquiring module 71 includes an acquiring sub-module 711 and a reconstructing sub-module 712. The acquiring sub-module 711 is configured to acquire a two-dimensional scanned image of the positioning and tracking member captured by a medical imaging device. The reconstructing sub-module 712 is configured to acquire the three-dimensional medical model by performing three-dimensional reconstruction on the two-dimensional scanned image.

Optionally, the segmenting module 72 includes a segmenting sub-module 721 and a determining sub-module 722. The segmenting sub-module 721 is configured to acquire a binarization model by performing threshold segmentation on the three-dimensional medical model based on eigenvalues of various voxels in the three-dimensional medical model. The determining sub-module 722 is configured to determine the plurality of the candidate connected regions based on non-zero voxels in the binarization model.

Optionally, the three-dimensional medical model includes a plurality of layers. The determining sub-module 722 is configured to determine non-zero voxels in the plurality of layers in the binarization model by traversing the plurality of layers in the binarization model; and determine the plurality of candidate connected regions based on coordinates of the non-zero voxels.

Optionally, the three-dimensional medical model is a three-dimensional medical model of CT, and the eigenvalues are CT values.

Optionally, the determining module 73 is configured to compare the geometrical information of each of the candidate connected regions with an actual size of the marker; and determine a candidate connected region where a difference value between the geometrical information and the actual size is within a predetermined range, of the plurality of candidate connected regions, as the target connected region.

Optionally, the apparatus may further include a filtering module 74 configured to filter the three-dimensional medical model before the segmenting module acquires the plurality of candidate connected regions by performing image segmentation on the three-dimensional medical model.

It should be noted that during the recognition of the marker, the apparatus for recognizing the marker according to the embodiments described above is merely illustrated by taking the dividing way of various functional modules described above as an example. In practical application, functions described above may be allocated to be implemented by different functional modules, that is, an internal structure of the apparatus may be divided into different functional modules to achieve all or a part of the functions described above. In addition, the apparatus for recognizing the marker according to the embodiments described above and the embodiments of the method for recognizing the marker belong to the same concept, and for specific implementation processes, reference is made to the method embodiments, which are not repeated herein.

According to an embodiment of the present disclosure, a storage medium is further provided. The storage medium is a computer readable medium storing a computer program. The computer program, when run by a processor, causes the processor to perform the methods as defined in the embodiments of the present disclosure.

Figure 8:
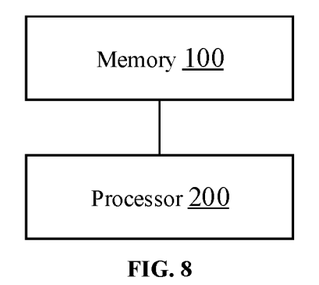
FIG. 8 shows a schematic structural diagram of an electronic device according to an embodiment of the present disclosure.

According to an embodiment of the present disclosure, an electronic device is further provided. A schematic structural diagram of the electronic device may be as shown in FIG. 8. The electronic device at least includes a memory 100 and a processor 200. The memory 100 stores a computer program therein. The processor 200, when running the computer program in the memory 100, is caused to perform the method as defined in any of the embodiments of the present disclosure.

In practical implementation, the electronic device may be a medical imaging device such as a CT machine, an X-ray machine, etc., or may be other electronic devices, such as a computer terminal, a tablet terminal, etc., which perform data communication with the medical imaging device, as long as the methods described above can be implemented correspondingly.

In this embodiment, by placing the positioning and tracking member on the body of the patient directly, a rigid connection between the positioning and tracking member and the human body is avoided, thereby avoiding damages to the human body. Furthermore, in conjunction with the algorithm for recognizing the marker, recognition of the marker in the image space is achieved rapidly by comparing geometrical information of various candidate connected regions in the three-dimensional medical model with the actual size of the marker, with fast recognition speed and high recognition accuracy.

The storage medium described above may be included in the electronic device described above; or may exist independently and is not assembled into the electronic device.

It should be noted that the storage medium described above in the present disclosure may be a computer readable signal medium or a computer readable storage medium or any combination thereof. The computer readable storage medium may include, for example, but is not limited to, an electrical, magnetic, optical, electromagnetic, infrared, or semiconducting system, apparatus, assembly, or any combination thereof. More specific examples of the computer readable storage medium may include but is not limited to: an electric connected computer disk having one or more conducting wires, a portable computer disk, a hard disk, a random-access memory (RAM), a read-only memory (ROM), an erasable programmable read-only memory (EPROM or a flash memory), a fiber-optic memory, a portable compact disc read-only memory (CD-ROM), an optical storage device, a magnetic storage device or any suitable combination thereof.

In the present disclosure, the computer readable storage medium may be any tangible medium including or storing a program. The program may be used by or in conjunction with an instruction executing system, apparatus, or device. However, in the present disclosure, the computer readable signal medium may include a data signal propagated in a base band or as a part of a carrier wave, wherein the data signal carries a computer readable program code. Such a propagated data signal may be in a plurality of forms, including but being not limited to an electromagnetic signal, an optical signal, or any suitable combination thereof. The computer readable signal medium may be any storage medium apart from the computer readable storage medium. The computer readable signal medium may send, propagate or transmit the program for use by or in conjunction with the instruction executing system, apparatus, or device. The program code included in the storage medium may be transmitted using any appropriate medium, including but being not limited to: an electric wire, an optical cable, radio frequency (RF), and the like or any suitable combination thereof.

System architectures, functions, and operations, that may be implemented by the systems, methods, and computer program products according to various embodiments of the present disclosure, are illustrated in flowcharts and block diagrams in the appended drawings. In this regard, each block of the flowcharts or block diagrams may represent a module, a program segment, or a part of a code, which includes one or more executable instructions for achieving specified logic functions. Further, it should be noted that in some alternative implementations, functions labeled in the blocks may also be achieved in a different order from those labeled in the appended drawings. For example, two connectively represented blocks may actually be executed substantially in parallel, or they may be executed in a reverse order sometimes, which depends on functions involved. It should be further noted that each block of the block diagrams and/or flowcharts and a combination of the blocks of the block diagrams and/or flowcharts may be implemented using a dedicated, hardware-based system which executes specified functions or operations, or may be implemented using a combination of dedicated hardware and computer instructions.

The functions described above in the present disclosure may be executed at least in part by one or more hardware logic components. For example, without limitation, exemplary types of hardware logic components that may be used include: a field-programmable gate array (FPGA), an application-specific integrated circuit (ASIC), an application specific standard product (ASSP), a system on a chip (SoC), a complex programmable logic device (CPLD) and the like. Various embodiments of the present disclosure are described above in detail, but the present disclosure is not limited to these specific embodiments. Many variations and modifications can be made by a person skilled in the art based on the concepts of the present disclosure. These variations and modifications should all fall within the scope of protection of the present disclosure.

What is claimed is:

1. A positioning and tracking member, comprising: a holding plate and a plurality of markers, wherein the holding plate comprises a first surface and a second surface that are opposite to each other, and the plurality of markers are disposed on the first surface, the second surface being configured to be adhered to a surface of a target object;
wherein the first surface is provided with a plurality of grooves, the plurality of grooves being in one-to-one correspondence with the plurality of markers; and
the markers are light-reflective spheres, wherein each of the light-reflective spheres comprises a sphere body and a base, the base comprising an arc-shaped base body and an outer flange disposed on an outer peripheral wall of the arc-shaped base body, the sphere body being made of a transparent material of a refractive index and fixed in the arc-shaped base body, and a reflecting layer being provided between the sphere body and the base;
wherein the arc-shaped base body of the light-reflective sphere is disposed within a corresponding groove in the plurality of grooves, and other part of the light-reflective sphere protrudes from the first surface.

2. The positioning and tracking member according to claim 1, wherein a difference between an eigenvalue of the holding plate in a medical image and an eigenvalue of the surface of the target object in the medical image is greater than a threshold.

3. The positioning and tracking member according to claim 1, wherein the holding plate is made of polyvinyl chloride.

4. The positioning and tracking member according to claim 1, wherein the plurality of markers are arranged in an array, and a spacing between any two adjacent markers of the plurality of markers is in a range of 15 mm to 50 mm.

5. A method for recognizing a marker, comprising:
acquiring a three-dimensional medical model of a positioning and tracking member, wherein the positioning and tracking member is adhered to a surface of a target object;

acquiring a plurality of candidate connected regions by performing image segmentation on the three-dimensional medical model; and determining, based on geometrical information of each of the candidate connected regions, a target connected region corresponding to the marker from the plurality of candidate connected regions;

wherein the positioning and tracking member comprises:
a holding plate and a plurality of markers, wherein the holding plate comprises a first surface and a second surface that are opposite to each other, and the plurality of markers are disposed on the first surface, the second surface being configured to be adhered to the surface of the target object;

wherein the first surface is provided with a plurality of grooves, the plurality of grooves being in one-to-one correspondence with the plurality of markers; and the markers are light-reflective spheres, wherein each of the light-reflective spheres comprises a sphere body and a base, the base comprising an arc-shaped base body and an outer flange disposed on an outer peripheral wall of the arc-shaped base body, the sphere body being made of a transparent material of a refractive index and fixed in the arc-shaped base body, and a reflecting layer being provided between the sphere body and the base;

wherein the arc-shaped base body of the light-reflective sphere is disposed within a corresponding groove in the plurality of grooves, and other part of the light-reflective sphere protrudes from the first surface.

6. The method according to claim 5, wherein acquiring the three-dimensional medical model of the positioning and tracking member comprises:

acquiring a two-dimensional scanned image of the positioning and tracking member captured by a medical imaging device; and acquiring the three-dimensional medical model by performing three-dimensional reconstruction on the two-dimensional scanned image.

7. The method according to claim 5, wherein acquiring the plurality of candidate connected regions by performing image segmentation on the three-dimensional medical model comprises:

acquiring a binarization model by performing threshold segmentation on the three-dimensional medical model based on eigenvalues of various voxels in the three-dimensional medical model; and determining the plurality of candidate connected regions based on non-zero voxels in the binarization model.

8. The method according to claim 7, wherein
the three-dimensional medical model comprises a plurality of layers; and determining the plurality of candidate connected regions based on the non-zero voxels in the binarization model comprises:
determining the non-zero voxels in a plurality of layers in the binarization model by traversing the plurality of layers in the binarization model; and
determining the plurality of candidate connected regions based on coordinates of the non-zero voxels.

9. The method according to claim 7, wherein the three-dimensional medical model is a three-dimensional medical model of computed tomography CT, and the eigenvalues are CT values.

10. The method according to claim 5, wherein determining, based on the geometrical information of each of the candidate connected regions, the target connected region corresponding to the marker from the plurality of candidate connected regions comprises:

comparing the geometrical information of each of the candidate connected regions with an actual size of the marker; and determining a candidate connected region, where a difference value between the geometrical information and the actual size is within a predetermined range, of the plurality of candidate connected regions, as the target connected region.

11. The method according to claim 5, wherein prior to acquiring the plurality of candidate connected regions by performing image segmentation on the three-dimensional medical model, the method further comprises:
filtering the three-dimensional medical model.

12. A non-transitory storage medium storing a computer program, wherein the computer program, when run by a processor, causes the processor to perform the method as defined in claim 5.

13. An electronic device for recognizing a marker, at least comprising a memory storing a computer program therein and a processor, wherein the processor, when running the computer program in the memory, is caused to perform a method for recognizing the marker;

wherein the method comprises:
acquiring a three-dimensional medical model of a positioning and tracking member, wherein the positioning and tracking member is adhered to a surface of a target object;

acquiring a plurality of candidate connected regions by performing image segmentation on the three-dimensional medical model; and determining, based on geometrical information of each of the candidate connected regions, a target connected region corresponding to the marker from the plurality of candidate connected regions;

wherein the positioning and tracking member comprises:
a holding plate and a plurality of markers, wherein the holding plate comprises a first surface and a second surface that are opposite to each other, and the plurality of markers are disposed on the first surface, the second surface being configured to be adhered to the surface of the target object;

wherein the first surface is provided with a plurality of grooves, the plurality of grooves being in one-to-one correspondence with the plurality of markers; and the markers are light-reflective spheres, wherein each of the light-reflective spheres comprises a sphere body and a base, the base comprising an arc-shaped base body and an outer flange disposed on an outer peripheral wall of the arc-shaped base body, the sphere body being made of a transparent material of a refractive index and fixed in the arc-shaped base body, and a reflecting layer being provided between the sphere body and the base;

wherein the arc-shaped base body of the light-reflective sphere is disposed within a corresponding groove in the plurality of grooves, and other part of the light-reflective sphere protrudes from the first surface.

14. The electronic device according to claim 13, wherein acquiring the three-dimensional medical model of the positioning and tracking member comprises:
acquiring a two-dimensional scanned image of the positioning and tracking member captured by a medical imaging device; and acquiring the three-dimensional medical model by performing three-dimensional reconstruction on the two-dimensional scanned image.

15. The electronic device according to claim 13, wherein acquiring the plurality of candidate connected regions by performing image segmentation on the three-dimensional medical model comprises:
   acquiring a binarization model by performing threshold segmentation on the three-dimensional medical model based on eigenvalues of various voxels in the three-dimensional medical model; and
   determining the plurality of candidate connected regions based on non-zero voxels in the binarization model.

16. The electronic device according to claim 15, wherein the three-dimensional medical model comprises a plurality of layers; and
   determining the plurality of candidate connected regions based on the non-zero voxels in the binarization model comprises:
      determining the non-zero voxels in a plurality of layers in the binarization model by traversing the plurality of layers in the binarization model; and
      determining the plurality of candidate connected regions based on coordinates of the non-zero voxels.

17. The electronic device according to claim 15, wherein the three-dimensional medical model is a three-dimensional medical model of computed tomography CT, and the eigenvalues are CT values.

18. The electronic device according to claim 13, wherein determining, based on the geometrical information of each of the candidate connected regions, the target connected region corresponding to the marker from the plurality of candidate connected regions comprises:
   comparing the geometrical information of each of the candidate connected regions with an actual size of the marker; and
   determining a candidate connected region, where a difference value between the geometrical information and the actual size is within a predetermined range, of the plurality of candidate connected regions, as the target connected region.

19. The electronic device according to claim 13, wherein prior to acquiring the plurality of candidate connected regions by performing image segmentation on the three-dimensional medical model, the method further comprises:
   filtering the three-dimensional medical model.

* * * * *